United States Patent
Haberland et al.

(10) Patent No.: US 10,947,545 B2
(45) Date of Patent: Mar. 16, 2021

(54) APTAMERS FOR USE IN INHIBITION AND/OR SUPPRESSION OF TLR9 ACTIVATION

(71) Applicant: Berlin Cures GmbH, Berlin (DE)

(72) Inventors: Annekathrin Haberland, Berlin (DE); Katrin Wenzel, Bernau (DE)

(73) Assignee: Berlin Cures GmbH, Berlin (DE)

( * ) Notice: Subject to any disclaimer, the term of this patent is extended or adjusted under 35 U.S.C. 154(b) by 0 days.

(21) Appl. No.: 16/349,396

(22) PCT Filed: Oct. 27, 2017

(86) PCT No.: PCT/EP2017/077675
§ 371 (c)(1),
(2) Date: May 13, 2019

(87) PCT Pub. No.: WO2018/095697
PCT Pub. Date: May 31, 2018

(65) Prior Publication Data
US 2019/0390199 A1  Dec. 26, 2019

(30) Foreign Application Priority Data
Nov. 23, 2016  (EP) .................................. 16200190

(51) Int. Cl.
*C12N 15/115* (2010.01)
*A61K 31/713* (2006.01)
*C12N 15/117* (2010.01)

(52) U.S. Cl.
CPC .......... *C12N 15/115* (2013.01); *A61K 31/713* (2013.01); *C12N 15/117* (2013.01); *C12N 2310/16* (2013.01)

(58) Field of Classification Search
CPC .... C12N 15/113; C12N 15/117; A61K 31/713
USPC ............... 435/91.1, 455, 458, 6.1, 91.31; 514/44 A; 536/23.1, 24.5
See application file for complete search history.

(56) References Cited

FOREIGN PATENT DOCUMENTS

| EP | 2468866 A1 * | 6/2012 | ........... C12N 15/117 |
| EP | 2468866 A1 | 6/2012 | |
| WO | 2005/037323 A2 | 4/2005 | |
| WO | WO-2005037323 A2 * | 4/2005 | ........... C12N 15/115 |
| WO | 2007/047396 A2 | 4/2007 | |
| WO | 2009/023819 A2 | 2/2009 | |

OTHER PUBLICATIONS

PCT International Search Report and Written Opinion for PCT Application No. PCT/EP2017/077675 dated Jan. 26, 2018 (12 pages).
European Search Report for EP Application No. 16200190.3 dated May 15, 2017 (5 pages).
European Office Action for EP Application No. 16200190.3 dated Jun. 2, 2017 (7 pages).
Fialova et al., "The Thrombin Binding Aptamer GGTTGGTGTGGTTGG Forms a Bimolecular Guanine Tetraplex," Biochemical and Biophysical Research Communications, 2006, 344:50-54.
Nadorp et al., "Gut Feeling: MicroRNA Discriminators of the Intestinal TLR9-Cholinergic Links," International Immunopharmacology, 2015, 29:8-14.
Wu et al., "In Vivo Efficacy of a Phosphodiester TLR-9 Aptamer and its Beneficial Effect in a Pulmonary Anthrax Infection Model," Cellular Immunology, 2008, 251:78-85.

* cited by examiner

*Primary Examiner* — Jane J Zara
(74) *Attorney, Agent, or Firm* — Eversheds Sutherland (US) LLP

(57) ABSTRACT

The present invention relates to new aptamer molecules for use in therapy of a subject by inhibiting or suppressing the activation of TLR9 in a cell, a method of inhibiting or suppressing the activation of TLR9 in a cell using such aptamer molecules, a pharmaceutical composition and a kit comprising such aptamer molecules and the use of aptamer molecules for inhibiting or suppressing TLR9 activation.

21 Claims, 5 Drawing Sheets
Specification includes a Sequence Listing.

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: Synthetic

<400> SEQUENCE: 1
ggttggtgtg gttgg                                                    15

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
tcgtcgtttt gtcgttttgt cgtt                                          24

<210> SEQ ID NO 3
<211> LENGTH: 10
<212> TYPE: DNA
<213> ORGANISM: Artificial Sequence
<220> FEATURE:
<223> OTHER INFORMATION: Synthetic

<400> SEQUENCE: 3
tggaggtgga                                                          10
```

```
<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
ttagggttag ggttagggtt aggg                                              24
```

APTAMERS FOR USE IN INHIBITION AND/OR SUPPRESSION OF TLR9 ACTIVATION

CROSS REFERENCE TO RELATED APPLICATIONS

This application claims the priority benefit of PCT/EP2017/077675 filed on Oct. 27, 2017 which claims priority benefit of European Application No. 16200190.3, filed Nov. 23, 2016, respectively. The entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on May 31, 2019, is named 42102864_1.txt and is 882 bytes in size.

TECHNICAL FIELD

The present invention relates to new aptamer molecules for use in therapy of a subject by inhibiting or suppressing the activation of TLR9 in a cell, a method of inhibiting or suppressing the activation of TLR9 in a cell using such aptamer molecules, a pharmaceutical composition and a kit comprising such aptamer molecules and the use of aptamer molecules for inhibiting or suppressing TLR9 activation.

BACKGROUND OF THE INVENTION

Toll-like receptors (TLRs) are present on many cells of the immune system and have been shown to be involved in the innate immune response (Hornung, V. et al., (2002) J. Immunol. 168:4531-4537). In vertebrates or mammals, this family consists of proteins called TLR1 to TLR10, which are known to recognize pathogen associated molecular patterns (PAMPs) from bacteria, fungi, parasites, and viruses (Poltorak, a. et al. (1998) Science 282:2085-2088; Underhill, D. M., et al. (1999) Nature 401:811-815; Hayashi, F. et. al (2001) Nature 410:1099-1103; Zhang, D. et al. (2004) Science 303:1522-1526; Meier, A. et al. (2003) Cell. Microbial. 5:561 570; Campos, M. A. et al. (2001) J. Immunol. 167: 416-423; Hoebe, K. et al. (2003) Nature 424: 743-748; Lund, J. (2003) J. Exp. Med. 198:513-520; Heil, F. et al. (2004) Science 303:1526-1529; Diebold, S. S., et al. (2004) Science 303:1529-1531; Hornung, V. et al. (2004) J. Immunol. 173:5935-5943).

TLRs are a key means by which mammals recognize and mount an immune response to foreign molecules and also provide a means by which the innate and adaptive immune responses are linked (Akira, S. et al. (2001) Nature Immunol. 2:675-680; Medzhitov, R. (2001) Nature Rev. Immunol. 1:135-145). TLRs have also been shown to play a role in the pathogenesis of many diseases, including autoimmunity, infectious disease, and inflammation (Cook, D. N. et al. (2004) Nature Immunol. 5:975-979) and the regulation of TLR mediated activation using appropriate agents may provide a means for disease intervention. Further, the triggering of TLR9 in plasmacytoid dendritic cells precursors (PDC) and B cells by self-nucleic acids has a significant role in the pathogenesis of Systemic Lupus Erythematosus (SLE).

As part of the defense against extra- and intracellular pathogens, TLRs are located at the cell surface but also inside the cell. While TLR2, 4, 5, and 6 are cell-surface located receptors defending the cell against the extracellular pathogens, TLR3, 7, 8, and 9 are generally located intracellularly in order to support the defense against intracellular pathogens (Dowling and Dellacasagrande, 2016) Dowling, J. K. and Dellacasagrande, J. (2016) Methods Mol. Biol. Clifton N.J. 1390, 3-27), (Diebold, S. S. et al. (2004) Science 303:1529-1531; Liew, F. et al. (2005) Nature 5:446-458; Hemmi H et al. (2002) Nat Immunol 3:196-200; Jurk M et al., (2002) Nat Immunol 3:499; Lee J et al. (2003) Proc. Natl. Acad. Sci. USA 100:6646-6651); (Alexopoulou, L. (2001) Nature 413:732-738).

Certain unmethylated CpG motifs present in bacterial and synthetic DNA have been shown to activate the immune system and induce antitumor activity through TLR 9 (Tokunaga T et al., J. Natl. Cancer Inst. (1984) 72:955-962; Shimada S, et al., Jpn. H cancer Res, 1986, 77, 808-816; Yamamoto S, et al., Jpn. J. Cancer Res., 1986, 79, 866-73). Mammalian DNA, in contrast, does not generally possess immunostimulatory activity due apparently to a low frequency of CG sequences and to most of the CG sequences having a methylated cytosine. Mammalian immune system cells thus appear to distinguish bacterial DNA from self DNA through the TLR9 receptor.

Other studies using antisense oligonucleotides containing CpG dinucleotides have been shown to stimulate immune responses (Zhao Q, et al. (1996) Biochem. Pharmacol. 26:173-182). Subsequent studies demonstrated that TLR9 recognizes unmethylated CpG motifs present in bacterial and synthetic DNA (Hemmi, H. et al. (2000) Nature 408: 740-745).

Other modifications of CpG-containing phosphorothioate oligonucleotides can also affect their ability to act as modulators of immune response through TLR9 (see, e.g., Zhao et al., Biochem. Pharmacol. (1996) 51:173-182; Zhao et al. (1996) Biochem Pharmacol. 52:1537-1544; Zhao et al. (1997) Antisense Nucleic Acid Drug Dev. 7:495-502; Zhao et al (1999) Bioorg. Med. Chem. Lett. 9:3453-3458; Zhao et al. (2000) Bioorg. Med. Chem. Lett. 10:1051-1054; Yu, D. et al. (2000) Bioorg. Med. Chem. Lett. 10:2585-2588; Yu, D. et al. (2001) Bioorg. Med. Chem. Lett. 11:2263-2267; and Kandimalla, E. et al. (2001) Bioorg. Med. Chem. 9:807-813).

In addition, structure activity relationship studies have allowed identification of synthetic motifs and novel DNA-based compounds that induce specific immune response profiles that are distinct from those resulting from unmethylated CpG dinucleotides (Kandimalla, E. et al. (2005) Proc. Natl. Acad. Sci. US A 102:6925-6930. Kandimalla, E. et al. (2003) Proc. Nat. Acad. Sci. US A 100:14303-14308; Cong, Y. et al. (2003) Biochem Biophys Res. Commun. 310: 1133-1139; Kandimalla, E. et al. (2003) Biochem. Biophys. Res. Commun. 306:948-953; Kandimalla, E. et al. (2003) Nucleic Acids Res. 31:2393-2400; Yu, D. et al. (2003) Bioorg. Med. Chem. 11:459-464; Bhagat, L. et al. (2003) Biochem. Biophys. Res. Commun. 300:853-861; Yu, D. et al. (2002) Nucleic Acids Res. 30:4460-4469; Yu, D. et al. (2002) J. Med. Chem. 45:4540-4548. Yu, D. et al. (2002) Biochem. Biophys. Res. Commun. 297:83-90; Kandimalla. E. et al. (2002) Bioconjug. Chem. 13:966-974; Yu, D. et al. (2002) Nucleic Acids Res. 30:1613-1619; Yu, D. et al. (2001) Bioorg. Med. Chern. 9:2803-2808; Yu, D. et al. (2001) Bioorg. Med. Chem. Lett. 11:2263-2267; Kandimalla, E. et al. (2001) Bioorg. Med. Chem. 9:807-813; Yu, D. et al. (2000) Bioorg. Med. Chem. Lett. 10:2585-2588; Putta, M. et al. (2006) Nucleic Acids Res. 34:3231-3238).

While activation of TLRs is involved in mounting an immune response, an uncontrolled stimulation of the immune system through TLRs may exacerbate certain diseases e.g. in immune-compromised subjects. Thus, in cases of generally or specifically increased immune answer caused by TLR 9 activation, the application of TLR9 antagonists may be desirable.

In recent years, several groups have shown the use of synthetic oligodeoxyoligonucleotides (ODNs) acting as inhibitors of inflammatory cytokines (Lenert, P. et al. (2003) DNA Cell Biol. 22(10):621-631).

Using certain synthetic ODNs, Lenert et al. report the ability to produce inhibitory ODNs (Lenert, P. et al. (2003) DNA Cell Biol. 22(10):621-631). These inhibitory ODN require two triplet sequences, a proximal "CCT" triplet and a distal "GGG" triplet. In addition to these triplet-containing inhibitory ODNs, several groups have reported other specific DNA sequences that could inhibit TLR 9-mediated activation by CpG-containing ODNs. These "inhibitory" or "suppressive" motifs are rich in poly "G" (e.g. "GGGG") or "GC" sequences, tend to be methylated, and are present in the DNA of mammals and certain viruses (see e.g., Chen, Y., et al., Gene Ther. 8: 1024-1032 (2001); Stunz, L. L., Eur. J. Immunol. 32: 1212-1222 (2002).

Duramad, O., et al., J. Immunol., 174: 5193-5200 (2005) and US patent application US 2005/0239733, describe a structure for inhibitory DNA oligonucleotides containing a GGGG motif within the sequences. Patole et al. demonstrate that GGGG containing ODNs will suppress systemic lupus (Patole, P. et al. (2005) J. Am. Soc. Nephrol. 16:3273-3280). Additionally, Gursel, I., et al., J. Immunol., 171: 1393-1400 (2003), describe repetitive TTAGGG elements, which are present at high frequency in mammalian telomeres and down-regulate CpG-induced immune activation. Shirota, H., et al., J. Immunol., 173: 5002-5007 (2004), demonstrate that synthetic oligonucleotides containing the TTAGGG element mimic this activity and could be effective in the prevention/treatment of certain Th1-dependent autoimmune diseases.

U.S. patent application Ser. No. 11/549,048 discloses a novel class of TLR antagonists that do not require a poly G sequence. Kandimalla et al. also describes the application of these novel compositions to treating and preventing various diseases and disorders (Ser. Nos. 11/549,048; 11/743,876; 12/140,334; 12/140,338; 12/244,199).

However, a challenge remains to develop additional TLR antagonists that do not require a poly G sequence. The number of TLR9 antagonists is still rather limited and their effectiveness and harmlessness for the application in humans or animals remains to be confirmed. The availability of additional TLR9 antagonists which show advantageous inhibition profiles is therefore desired.

Such new custom compounds and compositions will find use in many clinically relevant applications, including treating and preventing for example diseases and disorders with an immune stimulatory component as well as pain and inflammation. Such compounds and compositions are currently tested for efficacy in asthma and allergic rhinitis or other allergic conditions (Basith S, Manavalan B, Lee G, Kim S G, Choi S. "Toll-like receptor modulators: a patent review (2006-2010)." *Expert Opin Ther Pat.* June 2011: 927-944.).

Many more diseases have been associated with an undesired or unnatural activation of TLR 9 in patients. It has also been known that cardiac fibroblasts carry the TLR9 receptor and that activation of the cardiac fibroblast TLR9 receptors seems to be involved in pathological heart conditions such as the myocarditis supporting a pathological situation (Ohm I K, Alfsnes K, Belland Olsen M, Ranheim T, Sandanger Ø, Dahl T B, Aukrust P, Finsen A V, Yndestad A, Vinge L E. "Toll-like receptor 9 mediated responses in cardiac fibroblasts." *PLoS One.* No date: e104398.).

A blockage, suppression or inhibition of TLR9 activation may, in such cases, show a therapeutic effect as already observed with IRS 954 from Dynavax in experimental lupus (Pawar R D1, Ramanjaneyulu A, Kulkarni O P, Lech M, Segerer S, Anders H J. "Inhibition of Toll-like receptor-7 (TLR-7) or TLR-7 plus TLR-9 attenuates glomerulonephritis and lung injury in experimental lupus." *J Am Soc Nephrol.* June 2007: 1721-1731.).

Only a very limited number of aptamers which could be used to regulate TLR 9 activation in, for example, autoimmune diseases is available at present and their effectiveness and harmlessness for the application in human patients remains to be confirmed. The availability of additional oligonucleotide sequences which inhibit or suppress TLR 9 activation is therefore desired.

Accordingly, it is an object of the present invention to provide new antagonists for the use in therapy of a subject by inhibiting or suppressing the activation of TLR9 in a cell.

Furthermore, it is another object of the present invention to provide a method for inhibiting or suppressing TLR9 activation employing new TLR9 antagonists.

It is also an object of the present invention to provide a pharmaceutical composition and a kit is comprising new TLR 9 antagonists.

It is a further object of the present invention to provide a use of novel TLR 9 antagonists for inhibiting or suppressing TLR9 activation.

SUMMARY OF THE INVENTION

This object is solved by the aspects of the present invention as specified hereinafter.

According to the first aspect of the present invention, an aptamer is provided for use in therapy of a subject by inhibiting or suppressing the activation of TLR9 in a cell.

In a preferred embodiment of the first aspect of the invention, the subject is a mammal, preferably the subject is a human.

In another preferred embodiment of the first aspect of the invention, the cell to be contacted and/or the subject to be treated is showing TLR9 overexpression and/or overactivity of TLR9-mediated signaling.

In yet another preferred embodiment of the first aspect of the invention, the cell and/or subject to be treated is tested for TLR9 overexpression and/or overactivity of TLR9-mediated signaling before inhibiting the activation of TLR 9 in the cell and/or subject.

In a preferred embodiment of the first aspect of the invention, the cell is a glial cell, microglial cell, astrocyte, macrophage, B cell and/or dendritic cell, preferably plasmacytoid dendritic cell.

In another preferred embodiment of the first aspect of the invention, the subject is having a disorder selected from an autoimmune disorder, an inflammatory disorder, an autoimmune connective tissue disease (ACTD) and/or a neurodegenerative disorder, preferably the disorder is selected from but not limited to psoriasis, rheumatoid arthritis, alopecia universalis, acute disseminated encephalomyelitis, Addison's disease, allergy, ankylosing spondylitis, antiphospholipid antibody syndrome, arteriosclerosis, atherosclerosis, autoimmune hemolytic anemia, autoimmune hepatitis, Bullous pemphigoid, Chagas' disease, chronic obstructive pulmonary disease, coeliac disease, cutaneous lupus erythematosus (CLE), dermatomyositis, diabetes, dilated cardiomyopathy (DCM), endometriosis, Goodpasture's syndrome, Graves' disease, Guillain-Barre syndrome, Hashimoto's disease, hidradenitis suppurativa, idiopathic thrombocytopenic purpura, inflammatory bowel disease, interstitial cystitis, morphea, multiple sclerosis (MS), myasthenia gravis, myocarditis, narcolepsy, neuromyotonia, pemphigus, pernicious anaemia, polymyositis, primary biliary cirrhosis, rheumatoid arthritis (RA), schizophrenia, Sjogren's syndrome, systemic lupus erythematosus (SLE), systemic sclerosis, temporal arteritis, vasculitis, vitiligo, vulvodynia, Wegener's granulomatosis, traumatic pain, neuropathic pain and acetaminophen toxicity.

In a preferred embodiment of the first aspect of the invention, the subject is having tumour/cancer, preferably the tumour/cancer is selected from the group consisting of breast cancer, cervical squamous cell carcinoma, gastric carcinoma, glioma, hepatocellular carcinoma, lung cancer, melanoma, prostate cancer, recurrent glioblastoma, recurrent non-Hodgkin lymphoma, colorectal cancer.

In one preferred embodiment of the first aspect of the invention, the aptamer comprises a nucleic acid sequence of SEQ ID No. 1 (GGT TGG TGT GGT TGG) and/or a nucleic acid sequence being at least 80% identical to SEQ ID No. 1.

According to the second aspect of the present invention, a method of inhibiting or suppressing the activation of TLR9 in a cell is provided comprising contacting a cell expressing TLR9 with an aptamer.

In a preferred embodiment of the second aspect of the invention, the method is carried out in vitro/ex vivo.

In another preferred embodiment of the second aspect of the invention, the method additionally comprises a previous step of testing the cell for TLR9 overexpression and/or overactivity of TLR9-mediated signaling.

In a preferred embodiment of the second aspect of the invention, the cell is a mammalian cell, preferably the cell is a human cell.

In one preferred embodiment of the second aspect of the invention, the aptamer comprises a nucleic acid sequence of SEQ ID No. 1 (GGT TGG TGT GGT TGG) and/or a nucleic acid sequence being at least 80% identical to SEQ ID No. 1.

According to the third aspect of the present invention, a pharmaceutical composition is provided comprising an aptamer for use according to the first aspect of the present invention and at least one pharmaceutically acceptable excipient.

According to the fourth aspect of the present invention, a kit is provided comprising at least one aptamer for use according to the first aspect of the present invention and a container.

According to the fifth aspect of the present invention, the use of the aptamer as defined herein for inhibiting or suppressing TLR9 activation is provided.

In a preferred embodiment of the fifth aspect of the invention, the aptamer is used in vitro/ex vivo.

DETAILED DESCRIPTION OF THE INVENTION

Figure 1:
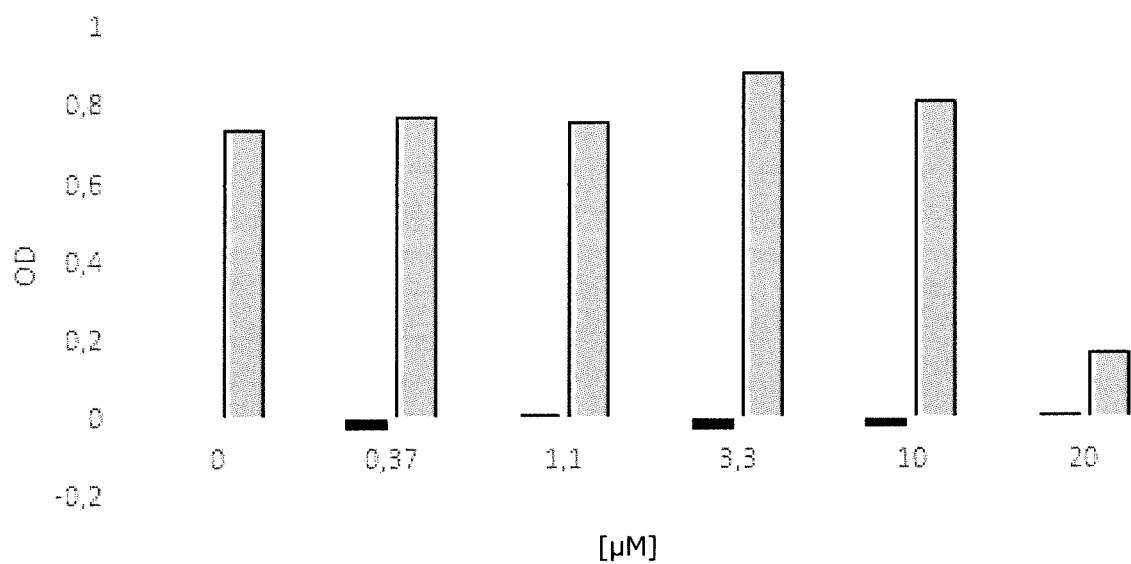
FIG. 1 shows the inhibition of TLR 9 activation in ODN 2006 (TLR 9 agonist)-stimulated HEK-Blue™ hTLR9 cells by adding increasing concentrations (in μM) of the aptamer of SEQ ID No. 1 (grey columns). Potential intrinsic effects of increasing concentrations of the aptamer of SEQ ID No. 1 on TLR 9 activation in the absence of stimulation by the TLR 9 agonist ODN 2006 (SEQ ID No. 2) were examined and are shown as black bars. Changes of optical density are caused by TLR 9-activated expression of an alkaline phosphatase.

The present invention is based on the identification of novel oligonucleotides of unexpected structure and nucleotide composition which are able to interact with and inhibit and suppress the activation of the TLR 9 receptor in eukaryotic cells.

Heretofore, only a very limited number of aptamers was known in the art which appear to have an antagonistic action with the TLR 9 receptor. Few common structural motifs are at the basis of the previously known antagonistic oligonucleotides. These common structures may in some cases however contribute to reduced bioavailability and/or other difficulties in view of the strict requirements for the pharmaceutical application of aptamers in therapy of, for example, human patients. To this end, it was highly desired to provide additional, structurally different aptamers for use in targeted modulation of TLR 9 activation.

The present inventors now identified for the first time the claimed aptamers as TLR 9 antagonists which are different from structural motifs of oligonucleotides commonly known to act antagonistically on the TLR 9 receptor. Thus, it now became possible to provide structurally novel oligonucleotides as TLR 9 antagonists.

According to one preferred embodiment of the present invention, the subject in which TLR 9 activation should be inhibited or suppressed is a vertebrate, more preferably the subject is a mammal. Within the meaning of the present invention, the group of mammals includes but is not limited to rats, mice, rabbits, cats, dogs, horses, cattle, cows, pigs, sheep, non-human primates and humans. Most preferably, the subject is a human.

Within the context of the present invention, it should be understood that any disclosure making reference only to a "subject" may additionally be read as the same disclosure referring to a "cell", and vice versa, unless the skilled person would consider such a disclosure to not make any technical sense.

According to another preferred embodiment of the present invention, at least one cell to be contacted with the aptamers of the invention is showing TLR9 overexpression. Thus, the subject to be treated with the aptamers of the invention is showing TLR 9 overexpression in at least some cells of this subject. More preferably, the subject to be treated is suffering from a disorder and/or symptoms caused by TLR 9 overexpression in at least some cells of said subject.

According to another preferred embodiment of the present invention, at least one cell to be contacted with the aptamers of the invention exhibits overactivity of TLR9-mediated signaling. This may mean that the subject to be treated with the aptamers of the invention is showing overactivity of TLR9-mediated signaling in at least some cells of this subject. More preferably, the subject to be treated is suffering from a disorder and/or symptoms caused by overactivity of TLR9-mediated signaling in at least some cells of said subject.

According to one preferred embodiment of the present invention, the cell and/or subject to be treated is tested for TLR9 overexpression and/or overactivity of TLR9-mediated signaling before inhibiting the activation of TLR 9 in the cell and/or subject. Thus, according to another preferred embodiment of the present invention, the cells and/or subjects to be treated have been characterized as showing TLR 9 overexpression and/or overactivity of TLR 9-mediated signalling prior to being contacted with or treated with the aptamers of the invention.

According to another preferred embodiment of the present invention, the subject to be treated is tested positive for TLR9 overexpression and/or overactivity of TLR9-mediated signalling.

It is well within the skilled person's capacities to reliably test and determine if a cell or a subject shows TLR9 overexpression and/or overactivity of TLR9-mediated signalling. In this context, reference is exemplarily made to the disclosure of Deering and Orange, Clin Vaccine Immunol. 2006 January; 13(1):68-76. Therein, methods for evaluation of TLR9 expression and/or activity of TLR9-mediated signaling are presented. Further evidence for TLR9 expression/activity evaluation forming part of the state of the art may be taken from the development of TLR9 Test Strip 2216 by Invivogen, San Diego, Calif., United States.

According to one preferred embodiment of the present invention, TLR9 overexpression and/or overactivity of TLR9-mediated signaling is assumed if TLR9-mediated production of TNFα is increased over a reference value for healthy subjects. According to a preferred embodiment, the value for the subject to be treated is determined as follows:

Determination of TLR9 Overexpression and/or Overactivity of TLR9-Mediated Signalling by Using TLR9-Mediated TNFα Production as a Surrogate Parameter Isolation of TLR9-Carrying Peripheral Blood Mononuclear Cells (PBMCs)

For estimating the TLR9 status of a patient, patients' PBMCs which carry the TLR9 receptor, are isolated from a sample of heparinized blood using Ficoll-Paque Plus density gradient separation (Amersham Biosciences, Uppsala, Sweden). Isolated PBMCs are resuspended in RPMI (GIBCO/BRL, Grand Island, N.Y.) containing 10% heat-inactivated fetal bovine serum (FBS; HyClone, Logan, Utah), 0.1 mM nonessential amino acids, 10 mM HEPES, 1 mM sodium pyruvate, 50 U/ml penicillin G, 50 µg/ml streptomycin sulfate, and 2 mM L-glutamine (GIBCO/BRL), altogether referred to as R10-FBS.

All media are filtered through disposable 0.2 µm filter (Millipore, Billerica, Mass.) after preparation. PBMCs can be cryopreserved by resuspending cells in 0.2 µm filter-sterilized FBS containing 10% dimethyl sulfoxide (DMSO; Fisher Scientific, Fair Lawn, N.J.) in a 1-ml polypropylene vial containing a neoprene gasket (Corning, Corning, N.Y.). Vials are gradually reduced in temperature by approximately 1° C./min using a methanol-containing non-mechanical cryopreservation unit (Nalgene, Rochester, N.Y.) in a −80° C. freezer. Prior to rapid thawing for use in an experiment, cells are stored in liquid nitrogen.

Upon thawing, cell viability is determined by trypan blue exclusion (GIBCO/BRL), and any sample with <95% viability is discarded.

Provoking Agonist (Ligand) Mediated TLR9 Response on PBMC's

TLR9 activity can be estimated when incubating the TLR9-receptor-containing PBMCs with the specific agonist/ligand ODN 2216. To provoke the TLR9 response, $2 \times 10^5$ PBMCs in 100 µl R10-FBS are added to each of the duplicate ligand-containing (40 µg ODN 2216/mL, 100 µL/well) or for control medium-containing wells and incubated at 37° C. for 24 h with 5% CO2. Ligand-free medium is used for determining the TNFα baseline production.

Estimation of the Amount of Formed TNFα Via Enzyme-Linked Immunosorbent Assay (ELISA)

The amount of TNFα, formed by ODN 2216 provoked PBMCs of patients' or control subjects' blood is estimated by TNFα-specific ELISA technique.

For this purpose, Immulon microtiter plates (ThermoLabSystems, Franklin, Mass.) are incubated overnight at 4° C. with 100 µl monoclonal anti-human TNFα capture antibody (BD Biosciences) in coating buffer (0.1 M sodium carbonate, pH 9.5). After discarding the supernatant, the plates are washed three times with phosphate-buffered saline (PBS) with 0.05% Tween 20 (PBST), pH 7.4, and afterwards blocked with PBS containing 10% bovine serum albumin, pH 7.0, for 1 h at room temperature.

The supernatants from individual wells of TLR9 ligand-stimulated PBMCs are transferred to individual antibody-coated wells.

It is preferred to dilute the supernatants twofold directly in the antibody-coated wells so that the amount of measured TNFα falls within a TNFα standard curve range in any case.

A serially diluted standard preparation of TNFα serves as the standard curve (R&D Systems, Minneapolis, Minn.).

After sample and standard curve loading, plates are incubated at room temperature for 2 h, followed by five washes using PBST. In order to detect the captured TNFα, 100 µl of a biotinylated anti-human TNFα sandwich monoclonal antibody (BD Biosciences) along with an avidin-horseradish peroxidase conjugate (BD Biosciences) has to be added to each well and the plates have to be incubated for 1 h at room temperature.

After washing five times with PBST and incubation with 100 µl tetramethylbenzidine plus hydrogen peroxide substrate solution for 30 min at room temperature, the colorimetric reaction is stopped by adding 50 µl of 1 M sulfuric acid. The absorbance is read at 450 nm using a microtiter plate spectrophotometer (Biotek, Winooski, Vt.).

According to one particular embodiment of the present invention, the value of TNFα as determined according to the method described hereinabove for the subject to be treated is at least 50 pg/ml, preferably at least 60 pg/ml, more preferably at least 75 pg/ml, even more preferably at least 90 pg/ml, even more preferably at least 100 pg/ml, even more preferably at least 110 pg/ml, even more preferably at least 125 pg/ml, even more preferably at least 150 pg/ml, most preferably at least 175 pg/ml.

In a preferred embodiment of the present invention, the cell to be contacted with the aptamers of the invention is a glial cell, microglial cell, astrocyte, macrophage, B cell and/or dendritic cell, more preferably a plasmacytoid dendritic cell. According to another more preferred embodiment, the cell to be contacted is a glial cell in the central nervous system.

In one preferred embodiment of the present invention, the subject is having a disorder selected from an autoimmune disorder, an inflammatory disorder, an autoimmune connective tissue disease (ACTD) and/or a neurodegenerative disorder, more preferably the disorder is selected from but not limited to psoriasis, rheumatoid arthritis, alopecia universalis, acute disseminated encephalomyelitis, Addison's disease, allergy, ankylosing spondylitis, antiphospholipid antibody syndrome, arteriosclerosis, atherosclerosis, autoimmune hemolytic anemia, autoimmune hepatitis, Bullous pemphigoid, Chagas' disease, chronic obstructive pulmonary disease, coeliac disease, cutaneous lupus erythematosus (CLE), dermatomyositis, diabetes, dilated cardiomyopathy (DCM), endometriosis, Goodpasture's syndrome, Graves' disease, Guillain-Barre syndrome, Hashimoto's disease, hidradenitis suppurativa, idiopathic thrombocytopenic purpura, inflammatory bowel disease, interstitial cystitis, morphea, multiple sclerosis (MS), myasthenia gravis, myocarditis, narcolepsy, neuromyotonia, pemphigus, pernicious anaemia, polymyositis, primary biliary cirrhosis, rheumatoid arthritis (RA), schizophrenia, Sjogren's syndrome, systemic lupus erythematosus (SLE), systemic sclerosis, temporal arteritis, vasculitis, vitiligo, vulvodynia, Wegener's granulomatosis, traumatic pain, neuropathic pain and acetaminophen toxicity.

In a more preferred embodiment, the subject is having an autoimmune disorder selected from the group including systemic lupus erythematosus, multiple sclerosis, arteriosclerosis, inflammatory bowel disease, diabetes, allergy and cancer, in particular autoimmune diabetes.

In another more preferred embodiment, the subject is having an autoimmune disorder which is associated with the presence of GPCR autoantibodies, even more preferably the autoimmune disorder is selected from the group comprising cardiomyopathy, dilated cardiomyopathy (DCM), ischemic cardiomyopathy (iCM), peripartum cardiomyopathy (PPCM), idiopathic cardiomyopathy, Chagas' cardiomyopathy, chemotherapy-induced cardiomyopathy, Chagas' megacolon, Chagas' megaesophagus, Chagas' neuropathy, benign prostatic hyperplasia, scleroderma, Raynaud syndrome, peripheral artery occlusive disease (PAOD), preeclamsia, kidney allograft rejection, myocarditis, glaucoma, hypertension, pulmonary hypertension, malignant hypertension, metabolic syndrome, Alopecia, Alopecia areata, migraine, Parkinson's disease, epilepsia, cluster headache, multiple sclerosis, depression, regional pain syndrome, instable angina pectoris, systemic lupus erythematosus (SLE), schizophrenia, Sjogren's syndrome, periodontitis, atrial fibrillation, vitiligo, hemolytic uremic syndrome, stiff person syndrome, congenital heart block, Diabetes mellitus Type I, psoriasis, Alzheimer's disease, fatigue, neurodermatitis, renal kidney disease, amyotrophic lateral sclerosis (ALS), Leber's hereditary optic neuropathy (LHON syndrome), allergic asthma, arrhythmia, refractory hypertension, Diabetes mellitus Type II, vascular dementia, non-Chagas megacolon and/or orthostatic hypertension.

In another more preferred embodiment, the subject suffers from a pathological heart condition, in particular from dilated cardiomyopathy and/or myocarditis.

In another more preferred embodiment of the present invention, the subject is having a neuropathic pain resulting from nerves affected by diabetes or chemotherapeutic drugs, from trauma, surgical procedures, arthritis, AIDS, burn injuries, cerebral or lumbar spine disease, fibromyalgia, post-eschemic pain, tumors, viral neuralgias, reflex sympathetic dystrophy syndrome, phantom limb and post-amputation pain, post-herpetic neuralgia, complex regional pain syndrome or central pain syndrome.

In another more preferred embodiment of the present invention, the subject is having an inflammation disorder such as rheumatoid arthritis, spondyloarthropathies, gouty arthritis, osteoarthritis, systemic lupus erythematosus, or juvenile arthritis. In another more preferred embodiment of the present invention, the subject is having inflammation associated with asthma, allergic rhinitis, sinus diseases, bronchitis, tuberculosis, acute pancreatitis, sepsis, infectious diseases, menstrual cramps, premature labor, tendinitis, bursitis, skin-related conditions such as psoriasis, eczema, atopic dermatitis, urticaria, dermatitis, contact dermatitis, and burns, or from post-operative inflammation including from ophthalmic surgery such as cataract surgery and refractive surgery, vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, allergic rhinitis, respiratory distress syndrome, systemic inflammatory response syndrome (SIRS), cancer-associated inflammation, reduction of tumor-associated angiogenesis, endotoxin shock syndrome, atherosclerosis, an ophthalmic disease, such as retinitis, retinopathies, uveitis, ocular photophobia, or acute injury to the eye tissue, pulmonary inflammation, such as that associated with viral infections or cystic fibrosis, chronic obstructive pulmonary disease, or acute respiratory distress syndrome, tissue rejection, graft v. host diseases, delayed-type hypersensitivity, as well as immune-mediated and inflammatory elements of CNS diseases such as Alzheimer's, Parkinson's, multiple sclerosis.

In another preferred embodiment of the present invention, the subject is having tumour/cancer, preferably the tumour/cancer is selected from the group consisting of breast cancer, cervical squamous cell carcinoma, gastric carcinoma, glioma, hepatocellular carcinoma, lung cancer, melanoma, prostate cancer, recurrent glioblastoma, recurrent non-Hodgkin lymphoma, colorectal cancer.

In another more preferred embodiment of the present invention, the subject is having acute lymphoblastic leukemia, acute myeloid leukemia, adrenocortical carcinoma, AIDS-related cancer, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gall bladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenstrom), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenstrom macroglobulinemia, and Wilms tumor (childhood).

In one preferred embodiment of the present invention, the aptamer sequences defined herein which cause an antagonistic effect on the TLR 9 receptor do not contain a cytosine nucleotide. It is evident that sequences which comprise a sequence having an antagonistic effect on TLR 9 may comprise additional nucleotide sequences including cytosine nucleotides.

In a more preferred embodiment of the present invention, the aptamer of the present invention disclosed and described herein comprises a nucleic acid sequence of SEQ ID No. 1 (GGT TGG TGT GGT TGG) and/or a nucleic acid sequence being at least 80% identical to SEQ ID No. 1. In another more preferred embodiment, the aptamer comprises the nucleic acid sequence of SEQ ID No. 1 (GGT TGG TGT GGT TGG), in particular the aptamer consists of the nucleic acid sequence of SEQ ID No. 1 (GGT TGG TGT GGT TGG).

In one preferred embodiment, the aptamer of the present invention as disclosed and described herein comprises a nucleic acid sequence of SEQ ID No. 5 (GGT TGG TGT GGT TG), preferably the aptamer consists of the nucleic acid sequence of SEQ ID No. 5 (GGT TGG TGT GGT TG).

The determination of percent identity between two sequences is accomplished according to the present invention by using the mathematical algorithm of Karlin and Altschul (Proc. Natl. Acad. Sci. USA (1993) 90: 5873-5877). Such an algorithm is the basis of the BLASTN and BLASTP programs of Altschul et al. (J. Mol. Biol. (1990) 215: 403-410). BLAST nucleotide searches are performed with the BLASTN program. To obtain gapped alignments for comparative purposes, Gapped BLAST is utilized as described by Altschul et al. (Nucleic Acids Res. (1997) 25: 3389-3402). When utilizing BLAST and Gapped BLAST programs, the default parameters of the respective programs are used.

According to a preferred embodiment of the present invention, aptamer sequences form part of the invention which consist of or comprise a nucleic acid sequence being at least 85% identical to the individualized aptamer sequences which are disclosed herein, more preferably at least 90% identical, even more preferred at least 95% identical.

For the purpose of this invention, the term "aptamer" refers to an oligonucleotide that binds specifically and with high affinity to a target molecule. Under defined conditions, aptamers may fold into a specific three dimensional structure. In one preferred embodiment of the present invention, the claimed aptamers interact specifically and with high affinity with the target receptor, more preferably with the TLR 9 receptor.

According to a preferred embodiment, the inventive aptamer does not form part of a nanostructure composed of a minimum of two components, wherein the minimum of two components are a plurality of oligonucleotides and a plurality of G-quadruplex forming nucleic acids linked to the plurality of oligonucleotides, more preferably the inventive aptamer does not form part of a nanostructure composed of a minimum of two components. Within this preferred embodiment, the two components are preferably structurally different. Further, within this preferred embodiment, a link between the plurality of oligonucleotides and the plurality of G-quadruplex forming nucleic acids linked to the plurality of oligonucleotides within the nanostructure disclaimed in this embodiment is either a covalent link or a non-covalent link, wherein the non-covalent link is more preferably based on one or more of electrostatic interactions, Van der Waals' forces, π-effects or hydrophobic effects.

According to another preferred embodiment, the inventive aptamer does not form part of a stable self-assembling nucleic acid nanostructure, comprising a plurality of oligonucleotides, wherein each internucleotide linkage of the oligonucleotide is not a phosphorothioate linkage, a plurality of G-quadruplex forming nucleic acids linked to the plurality of oligonucleotides, wherein the G-quadruplex forming nucleic acids is not TAGGGTT, and a plurality of G-quadruplex stabilizing domains linked to the G-quadruplex forming nucleic acids, wherein the oligonucleotides, the G-quadruplex forming nucleic acids and the G-quadruplex stabilizing domains form a plurality of G-quad structures.

According to another preferred embodiment, the inventive aptamer does not form part of a stable self-assembling nucleic acid nanostructure, comprising a plurality of oligonucleotides, a plurality of G-quadruplex forming nucleic acids linked to the plurality of oligonucleotides, wherein the G-quadruplex forming nucleic acids is not TAGGGTT, and a plurality of G-quadruplex stabilizing domains linked to the G-quadruplex forming nucleic acids, wherein when at least one of the G-quadruplex forming nucleic acids comprises GG, GGG, or GGGG and the oligonucleotide is CpG oligonucleotide the lipid is not diacyllipid, wherein the oligonucleotides, the G-quadruplex forming nucleic acids and the G-quadruplex stabilizing domains form a plurality of G-quad structures.

According to yet another preferred embodiment, the inventive aptamer does not form part of a nucleic acid nanostructure comprising G-quadruplex stabilizing domains linked to the inventive aptamer.

The aptamer of the invention comprises or consists of a sequence of nucleic acid molecules, the nucleotides. According to a preferred embodiment, the aptamer of the invention consists of a nucleotide sequence as defined herein.

The aptamer of the invention preferably comprises unmodified and/or modified D- and/or L-nucleotides. According to the common one letter code of nucleic acid bases "C" or stands for cytosine, "A" or stands for adenine, "G" or stands for guanine, and "T" or stands for thymine if the nucleotide sequence is a DNA sequence and "T" or stands for a uracil nucleotide if the nucleotide sequence is a RNA sequence. If not indicated below to the contrary, the term "nucleotide" shall refer to ribonucleotides and desoxyribonucleotides.

The aptamer of the invention can comprise or consist of a DNA- or an RNA-nucleotide sequence and, thus, can be referred to as DNA-aptamer or RNA-aptamer, respectively. It is understood that, if the aptamer of the invention comprises an RNA-nucleotide sequence, within the sequence motifs specified throughout the present invention "T" stands for uracil.

For the sake of conciseness throughout the present invention, reference is made solely to explicit DNA-nucleotide sequences. However, it is understood that the respective RNA-nucleotide sequences are also comprised by the present invention.

According to one embodiment, the use of DNA-aptamers is preferred. DNA-aptamers are usually more stable in plasma than RNA-aptamers. However, according to an alternative embodiment, RNA-aptamers are preferred. According to another embodiment, single strand nucleotide sequences are preferred. According to another alternative embodiment, double strand nucleotide sequences are preferred.

The aptamers of the invention may comprise a nucleotide sequence containing 2'-modified nucleotides, e.g. 2'-fluoro-, 2'-methoxy-, 2'-methoxyethyl- and/or 2'-amino-modified nucleotides. The aptamer of the invention may also comprise a mixture of desoxyribonucleotides, modified desoxyribonucleotides, ribonucleotides and/or modified ribonucleotides. Respectively, the terms "2'-fluoro-modified nucleotide", "2'-methoxy-modified nucleotide", "2'-methoxyethyl-modified nucleotide" and/or "2-amino-modified nucleotide" refer to modified ribonucleotides and modified desoxyribonucleotides.

The aptamer of the invention may comprise modifications. Such modifications encompass e.g. alkylation, i.e. methylation, arylation or acetylation of at least one nucleotide, the inclusion of enantiomers and/or the fusion of aptamers with one or more other nucleotides or nucleic acid sequences. Such modifications may comprise e.g. 5'- and/or 3'-PEG- or 5'- and/or 3'-CAP-modifications. Alternatively or in addition, the aptamer of the invention may comprise modified nucleotides, preferably selected from locked-nucleic acids, 2'-fluoro-, 2'-methoxy- and/or 2'-amino-modified nucleotides.

Locked nucleic acids (LNA) represent analogons of the respective RNA nucleotides wherein the conformation has been fixed. Oligonucleotides of locked nucleic acids comprise one or more bicyclic ribonucleosides, wherein the 2'-OH group is connected with the $C_4$-carbon atom via a methylen group. Locked nucleic acids exhibit an improved stability versus nucleases compared to the respective unmodified RNA-aptamer counterparts. Also the hybridization properties are improved which allows for an enhancement of affinity and specificity of the aptamer.

Another preferred modification is the addition of a so called 3'-CAP-, a 5'-CAP-structure and/or of a modified guanosin-nucleotide (e.g. 7-methyl-guanosin) to the 3'- and/or 5'-end of the aptamer. Such a modification of the 3'- and/or 5'-end has the effect that the aptamer is protected from a fast degradation by nucleases.

Alternatively or in addition, the aptamer of the invention can exhibit a pegylated 3' or 5'-end. A 3'- or 5'-PEG modification comprises the addition of at least one polyethylene glycol (PEG) unit, preferably the PEG group comprises 1 to 900 ethylene groups, more preferably from 1 to 450 ethylene groups. In a preferred embodiment, the aptamer comprises linear PEG units with HO—$(CH_2CH_2O)_n$—H, wherein n is an integer of 1 to 900, preferably n is an integer of 1 to 450.

The aptamer of the invention can be wholly or in part configured as a peptide nucleic acid (PNA). The aptamers according to the present invention may further be modified as described in Keefe A D et al., Nat Rev Drug Discov. 2010 July; 9(7):537-50 or in Mayer G, Angew Chem Int Ed Engl. 2009; 48(15):2672-89 or in Mayer, G. and Famulok M., Pharmazie in unserer Zeit 2007; 36: 432-436.

The term "oligonucleotide" generally refers to a polynucleoside comprising a plurality of linked nucleoside units. Such oligonucleotides can be obtained from existing nucleic acid sources, including genomic or cDNA, but are preferably produced by synthetic methods. In preferred embodiments each nucleoside unit can encompass various chemical modifications and substitutions as compared to wild-type oligonucleotides, including but not limited to modified nucleoside base and/or modified sugar unit.

Examples of chemical modifications are known to the person skilled in the art and are described, for example, in Uhlmann, E. et al. (1990) Chem. Rev. 90:543; "Protocols for Oligonucleotides and Analogs" Synthesis and Properties & Synthesis and Analytical Techniques, S. Agrawal, Ed, Humana Press, Totowa, USA 1993; and Hunziker, J. et al. (1995) Mod. Syn. Methods 7:331-417; and Crooke, S. et al. (1996) Ann. Rev. Pharm. Tox. 36:107-129.

The nucleoside residues can be coupled to each other by any of the numerous known internucleoside linkages, inter alia to improve stability of the oligonucleotides against enzymatic degradation, e.g. by nucleases. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages.

The term "oligonucleotide" also encompasses polynucleosides having one or more stereospecific internucleoside linkage (e.g., (Rr)- or (Sr)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate or phosphorodithioate linkages or combinations thereof, more preferably the internucleoside linkages are phosphorothioate.

Further, the aptamers may be encapsulated in suitable vehicles to protect their structural integrity as well as to promote their delivery inside cells. Preferred vehicles include liposomes, lipid vesicles, microparticles, and the like.

Lipid vesicles resemble plasma membranes, and they can be made to fuse with cell membranes. Most liposomes and multilamellar vesicles are not readily fusogenic, mainly because the stored energy of the vesicle radius of curvature is minimal. Preferred lipid vesicles include small unilamellar vesicles. The small unilamellar vesicles contemplated for encapsulating the aptamers of the present invention are very fusogenic, because they have a very tight radius of curvature. The average diameter of a small unilamellar vesicle is 5 nm to 500 nm; preferably 10 nm to 100 nm, more preferably 20 nm to 60 nm, including 40 nm. This size allows vesicles to pass through the gaps between endothelial cells, thereby permitting systemic delivery of aptamer-containing vesicles following intravenous administration. Useful vesicles may vary greatly in size and are selected according to a specific application with an aptamer.

Small unilamellar vesicles can be readily prepared in vitro using procedures available in the art (as for example disclosed in WO 2005/037323 A2). The compositions from which the vesicles are formed contain a phospholipid which is a stable vesicle former, preferably together with another polar lipid, and optionally with one or more additional polar lipids and/or raft formers. Preferred phospholipids that are stable vesicle formers include 1-palmitoyl-2-docosahexaenoyl-sn-glycero-3-phosphocholine and 1,2-dioleoyl-sn-glycero-3-phosphocholine. Preferred polar lipids include: 1-palmitoyl-2-oleoyl-sn-glycero-3-phosphate, 1,2-dioleoyl-sn-glycero-3-ethylphosphocholine, 1,2-dioleoyl-sn-glycero-3-phosphoethanolamine, 1,2-dioleoyl-sn-glycero-3-[phospho-1-serine], a typical sphingomyelin, 1,2-dimyristoyl-sn-glycerol, and 1-palmitoyl-2-hydroxy-sn-glycero-3-phosphocholine.

Other preferred polar lipids include phosphatidylserine, phosphatidylglycerol, mixed chain phosphatidylcholine, phosphatidylethanol, and phospholipids containing decosahexaenoic acids. One example of a preferred raft former is cholesterol.

One advantage of modifying the aptamer of the invention by one of the ways mentioned above is that the aptamer can be stabilized against detrimental influences like e.g. nucleases present in the environment wherein the aptamer is used. Said modifications are also suitable to adapt the pharmacological properties of the aptamer. The modifications preferably do not alter the affinity or specificity of the aptamer.

The aptamer of the invention may also be conjugated to a carrier molecule and/or to a reporter molecule. Carrier molecules comprise such molecules that, when conjugated to the aptamer, prolong the plasma half-life of the conjugated aptamer in human plasma, e.g. by enhancing the stability and/or by affecting the excretion rate. One example of a suitable carrier molecule is PEG.

Reporter molecules comprise molecules that allow for the detection of the conjugated aptamer. Examples of such reporter molecules are GFP, biotin, cholesterol, dyes like e.g. fluorescence dyes, electrochemically active reporter molecules and/or compounds comprising radioactive residues, in particular radionuclides suitable for PET (positron emission tomography) detection like e.g. $^{18}$F, $^{11}$C, $^{13}$N, $^{15}$O, $^{82}$Rb or $^{68}$Ga. The skilled person is well aware of suitable carrier and reporter molecules and of ways of how to conjugate them to the aptamer of the invention.

The aptamers of the present invention are useful for the treatment of certain diseases by inhibiting or suppressing the activation of TLR 9 in a cell. In the context of the present invention, the aptamers are considered to be useful for human subjects as well as for animal subjects. According to one embodiment, the aptamers are for use in human subjects. According to another embodiment, the aptamers are for use in animal subjects.

Diseases in which inhibition or suppression of the activation of TLR 9 may be useful are such that TLR 9 activation causes undesired symptoms or consequences in a subject exhibiting such TLR 9 activation. According to a preferred embodiment, the disorder and/or a disease is caused by TLR 9 activation in a subject to be treated. According to a particularly preferred embodiment, the disorder and/or a disease is caused by TLR 9 activation in a subject treated against autoantibodies directed at G-protein coupled receptors.

Several diseases have already been reported or are known in the literature to be associated with TLR 9 activation. The present inventors have conducted further research in view of such an association and have discovered that more diseases than previously reported may be associated with such TLR 9 activation or TLR 9 overactivation (data not shown).

Due to the affinity of the claimed aptamers to TLR 9 and their antagonistic effects thereon, any disease which is associated with the activation or overactivation of TLR 9 is plausible to be effectively treated with the aptamers presented and claimed herein. Thus, in principle all of the diseases which have been recognized to be associated with TLR 9 (over)activation are promising target diseases to be treated with the aptamers according to the present invention.

The aptamers of the present invention are capable to cause an effect on the TLR 9 receptor, preferably an antagonistic effect thereon. Thus, in a preferred embodiment, the claimed aptamers act as TLR 9 antagonists. Preferably, the claimed aptamers are capable to inhibit or suppress TLR 9 activation. According to one preferred embodiment, the aptamers of the present invention do not exhibit an effect on the TLR 7 receptor, more preferably they do not exhibit an effect on any other TLR receptor molecule. According to a different preferred embodiment, the aptamers of the present invention also exhibit an effect on the TLR 7 receptor.

By inhibiting the pathological or undesired activation or overactivation of the TLR 9 receptor, the potentially negative effects of TLR 9 activation are neutralized and diminished and the permanent or temporary activation of TLR 9 may be abolished or reduced to normal levels. As a consequence, the extent and gravity of a disease caused or associated with TLR 9 activation may be significantly reduced. Thus, the present invention provides aptamers that are suitable for use in treatment of diseases associated with TLR 9 activation or overactivation.

According to another embodiment of the present invention, a method of inhibiting or suppressing the activation of TLR9 in a cell is provided comprising contacting a cell expressing TLR9 with an aptamer.

In a preferred embodiment of the present invention, the method is carried out in vitro/ex vivo. More preferably, the cell to be contacted with an aptamer according to the method of the present invention does not form part of a whole living organism. In one embodiment, the cell to be contacted may be cultured in cell culture. Such cultures of individual or groups of cells may be carried out as usually done in the art.

In another preferred embodiment of the method of the present invention, the method may be carried out in vivo and/or on cells which form part of a whole living organism. According to this embodiment, the method preferably comprises an additional, previous step of testing the cell/s to be contacted for TLR9 activation, more preferably the cell/s is/are tested for TLR 9 overexpression and/or overactivity of TLR9-mediated signaling.

In a preferred embodiment of the second aspect of the invention, the cell is a mammalian cell, preferably the cell is a human cell.

The present invention is also directed to a pharmaceutical composition comprising at least one aptamer of the invention and, optionally, at least one pharmaceutically acceptable excipient. The invention is also directed to a pharmaceutical composition comprising an aptamer of the invention or a mixture of different aptamers of the invention and a pharmaceutically acceptable excipient like e.g. a suitable carrier or diluent.

Preferably, the aptamer of the invention constitutes an active ingredient of the pharmaceutical composition and/or is present in an effective amount. The term "effective amount" denotes an amount of the aptamer of the invention having a prophylactically, diagnostically or therapeutically relevant effect on a disease or pathological condition. A prophylactic effect prevents the outbreak of a disease. A therapeutically relevant effect relieves to some extent one or more symptoms of a disease or returns to normal either partially or completely one or more physiological or biochemical parameters associated with or causative of the disease or pathological conditions.

The respective amount for administering the aptamer of the invention is sufficiently high in order to achieve the desired prophylactic, diagnostic or therapeutic effect. It will be understood by the skilled person that the specific dose level, frequency and period of administration to any particular mammal will depend upon a variety of factors including the activity of the specific components employed, the age, body weight, general health, sex, diet, time of administration, route of administration, drug combination, and the severity of the specific therapy. Using well-known means and methods, the exact amount can be determined by one of skill in the art as a matter of routine experimentation.

According to one embodiment of the pharmaceutical composition of the invention at least 20% of the total aptamer content is made of an aptamer of the invention, preferably at least 50%, more preferably at least 75%, most preferable at least 95%.

When used for therapy, the pharmaceutical composition will generally be administered as a formulation in association with one or more pharmaceutically acceptable excipients. The term "excipient" is used herein to describe any ingredient other than the aptamer of the invention. The choice of excipient will to a large extent depend on the particular mode of administration. Excipients can be suitable carriers and/or diluents.

The pharmaceutical composition of the invention may be administered orally. Oral administration may involve swallowing, so that the composition enters the gastrointestinal tract, or buccal or sublingual administration may be employed by which the composition enters the blood stream directly from the mouth.

Formulations suitable for oral administration include: solid formulations such as tablets; coated tablets, capsules containing particulates, liquids, or powders; lozenges (including liquid-filled); and chews; multi- and nano-particulates; gels; solid solutions; liposomes; films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

For tablet dosage forms, depending on dose, the aptamer of the invention may make up from 0.1 weight % to 80 weight % of the dosage form, more typically from 5 weight % to 60 weight % of the dosage form. In addition to the aptamer of the invention, tablets generally contain a disintegrant.

Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate.

Generally, the disintegrant will comprise from 1 weight % to 25 weight %, preferably from 5 weight % to 20 weight % of the dosage form.

Tablets may comprise additional excipients like e.g. binders, surface active agents, lubricants and/or other possible ingredients like e.g. anti-oxidants, colorants, flavouring agents, preservatives and/or taste-masking agents.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

Solid formulations for oral administration may be formulated to be immediate and/or modified release. Modified release formulations include delayed-, sustained-, pulsed-, controlled-, targeted and programmed release.

The pharmaceutical composition of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of pharmaceutical composition of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLApoly(dl-lactic-coglycolic)acid (PGLA) microspheres.

The pharmaceutical composition of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions.

Liposomes may also be used. Typical carriers include alcohol, water, mineral oil, liquid petrolatum, white petrolatum, glycerin, polyethylene glycol and propylene glycol. Penetration enhancers may be incorporated. Other means of topical administration include delivery by electroporation, iontophoresis, phonophoresis, sonophoresis and microneedle or needle-free (e.g. Powderject™, Bioject™, etc.) injection. Formulations for topical administration may be formulated to be immediate and/or modified release. Modified release formulations include delayed-, sustained-, pulsed-, controlled-, targeted and programmed release.

For administration to human patients, the total daily dose of the aptamer of the invention and/or the pharmaceutical composition of the invention is typically in the range 0.001 mg to 5000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 75 kg to 80 kg. The physician will readily be able to determine doses for subjects whose weight falls outside this range, such as infants and the elderly.

In the context of the present invention, the aptamer may preferably be administered in combination with one or more vaccines, antigens, antibodies, cytotoxic agents, allergens, antibiotics, antisense oligonucleotides, TLR antagonist, peptides, proteins, gene therapy vectors, DNA vaccines, adjuvants or kinase inhibitors.

The present invention also encompasses a kit comprising an aptamer of the invention, a container and optionally written instructions for use and/or with means for administration.

For treatment and/or diagnosis of a disease, irrespective of the route of administration, the aptamer of the invention is administered at a daily dose per treatment cycle of not more than 20 mg/kg body weight, preferably of not more than 10 mg/kg body weight, more preferably selected from the range of 1 µg/kg to 20 mg/kg body weight, most preferably selected from a range of 0.01 to 10 mg/kg body weight.

In a preferred embodiment of the present invention, the aptamer may be used in vitro/ex vivo. In an alternative preferred embodiment, the aptamer may be used in vivo.

The manufacturing or mass production of aptamers of the invention is well known in the art and represents a mere routine activity.

All embodiments of the present invention as described herein are deemed to be combinable in any combination, unless the skilled person considers such a combination to not make any technical sense.

EXAMPLES

Functional Assay for the Estimation of an Antagonistic Effect of the Aptamers of the Invention on the TLR 9 Receptor A functional assay able to identify antagonistic effects of oligonucleotides on the TLR 9 receptor was established for the estimation of the capacity to inhibit or suppress TLR 9 activation.

This functional assay uses a recombinant HEK-293 cell line and an established TLR 9 agonist/antagonist assay (HEK-Blue™ hTLR9 from InvivoGen, San Diego, Calif., USA). The cell line used carries a functionally overexpressed human TLR9 receptor coupled to a reporter gene which is an alkaline phosphatase secreted upon signaling by an NFkB inducible promotor. The signal of TLR9 activation is an increased optical density value (OD).

A recombinant HEK-293 cells which carries the reporter gene, but not the TLR9 receptor serves as a control (HEK-Blue™ TNF-α cells from InvivoGen, San Diego, Calif., USA). Here, the reporter gene is activated via TNFα. Using this control cell, it can be distinguished if effects are specific for the TLR9 receptor, or if they are caused by an interference with the signal cascade.

Example 1

In this Example, the inhibitory effect of SEQ ID No. 1 (GGT TGG TGT GGT TGG) on the TLR 9 receptor is examined. HEK-Blue™ hTLR9 cells were preincubated with different concentrations of the aptamer of SEQ ID No. 1 (0, 0.37, 1.1, 3.3, 10 and 20 µM of aptamer) for 60 minutes before 300 ng/ml (38.86 nM) of the well-known TLR 9 agonist ODN 2006 (SEQ ID No. 2: TCG TCG TTT TGT CGT TTT GTC GTT) were added and cells were incubated further for 18 hours. Subsequently, the optical density was determined using a standard alkaline phosphatase assay. Results of this assay are shown as grey columns in FIG. 1.

A potentially intrinsic effect of SEQ ID No. 1 on the signal cascade involving TLR 9 was also tested in the absence of the agonist ODN 2006 and is depicted as black columns in FIG. 1.

As a control, the same experimental setup was used employing HEK-Blue™ TNF-α cells as a control as described above. These TNF-α sensitive cells were preincubated with different concentrations of the aptamer of SEQ ID No. 1 (0, 0.37, 1.1, 3.3, 10 and 20 μM of aptamer) for 60 minutes before 100 ng/ml of TNF-α (with a MW of 17484 Dalton; final concentration of TNF-α: 5.7 nM) and cells were incubated further for 18 hours. Subsequently, the optical density was determined. Results of this assay are shown as grey columns in FIG. 2. A potentially intrinsic effect of SEQ ID No. 1 on the signal cascade involving TNF-α was also tested in the absence of the stimulatory molecule TNF-α and is depicted as black columns in FIG. 2.

Figure 2:
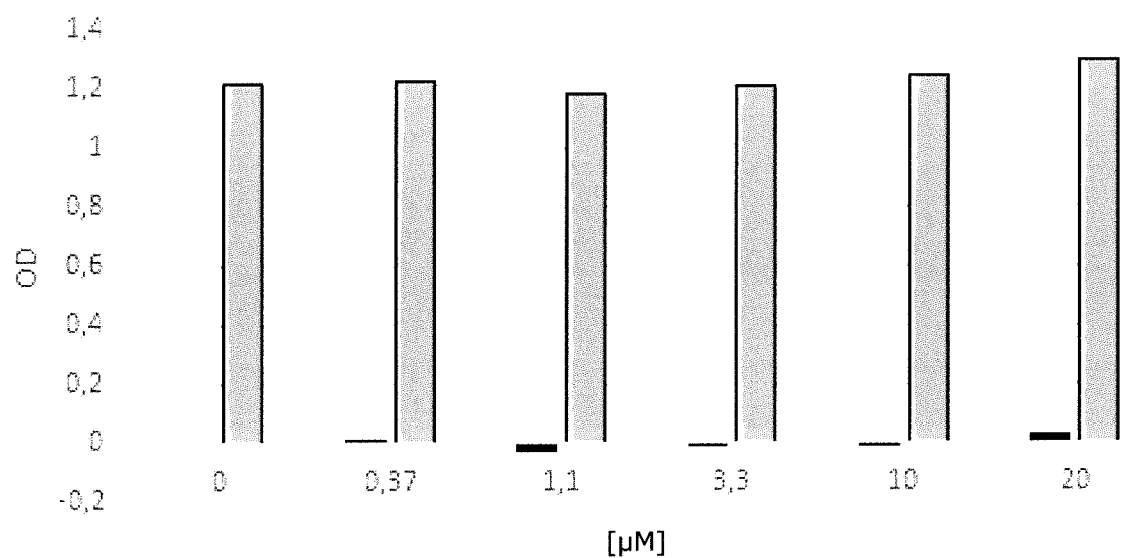
FIG. 2 shows effects of increasing concentrations of the aptamer of SEQ ID No. 1 (in μM) on HEK-Blue™ TNF-α cells stimulated with 100 ng of TNF-α (grey columns) and in the absence of stimulation by TNF-α (black columns). Changes of optical density are caused by TNF-α-activated expression of an alkaline phosphatase.

From these experiments and the results shown in FIGS. 1 and 2 it can be seen that the aptamer of SEQ ID No. 1 (GGT TGG TGT GGT TGG) has no intrinsic or non-specific effects on the agonist/antagonist assay or reporter expression but instead shows a clear inhibition and suppression of TLR 9 activation.

Example 2

As further control experiments, the assay described above and in Example 1 was used to determine potential inhibitory effects of a different oligonucleotide sequence. To this end, the same experiments including the controls as explained in Example 1 were carried out using SEQ ID No. 3 (TGG AGG TGG A) instead of SEQ ID No. 1 for comparison.

Figure 3:
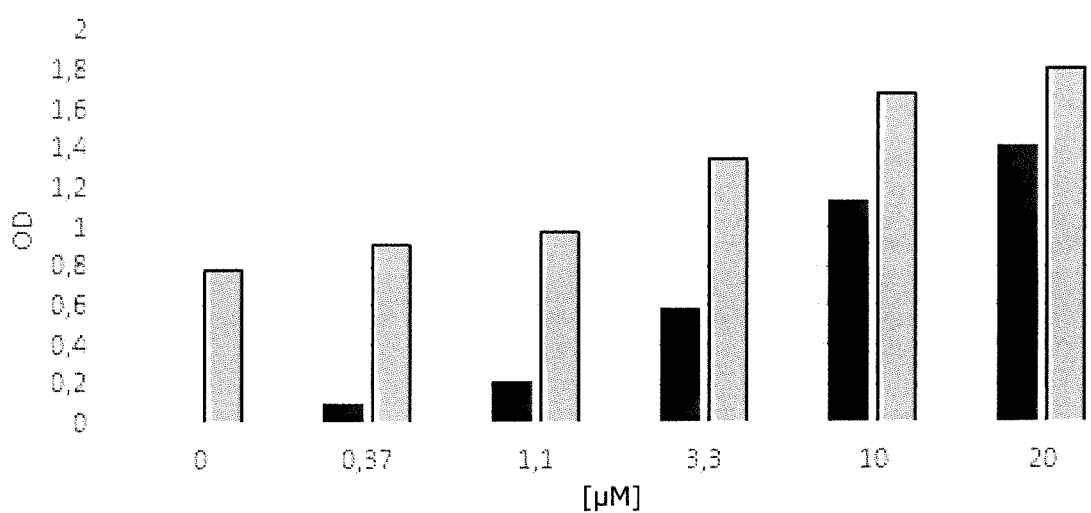
FIG. 3 shows the inhibition of TLR 9 activation in ODN 2006 (TLR 9 agonist)-stimulated HEK-Blue™ hTLR9 cells by adding increasing concentrations (in μM) of the aptamer of SEQ ID No. 3 (grey columns). Potential intrinsic effects of increasing concentrations of the aptamer of SEQ ID No. 3 on TLR 9 activation in the absence of stimulation by the TLR 9 agonist ODN 2006 (SEQ ID No. 2) were examined and are shown as black bars. Changes of optical density are caused by TLR 9-activated expression of an alkaline phosphatase.
Figure 4:
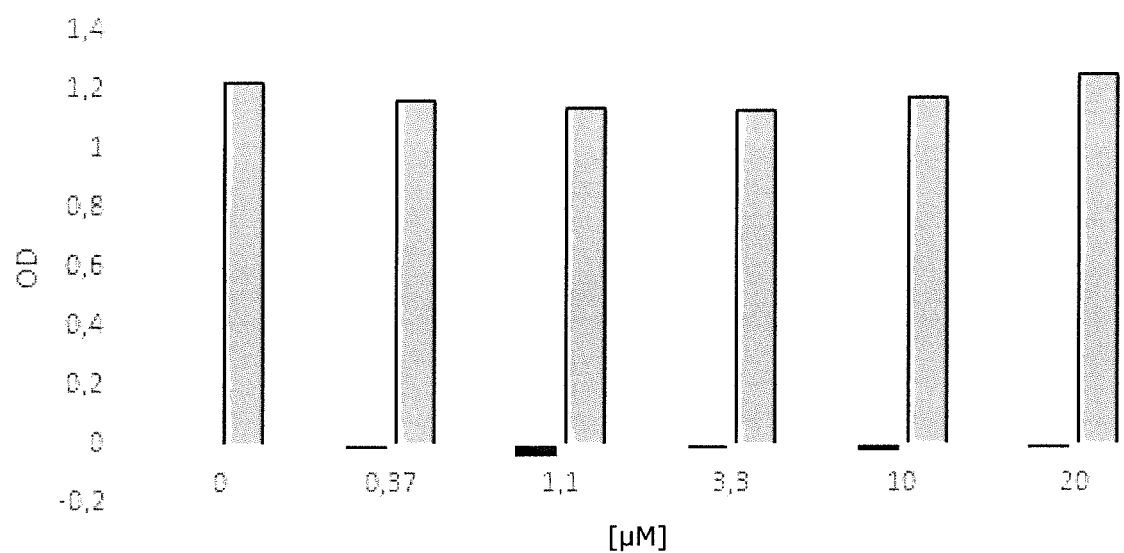
FIG. 4 shows effects of increasing concentrations of the aptamer of SEQ ID No. 3 (in μM) on HEK-Blue™ TNF-α cells stimulated with 100 ng of TNF-α (grey columns) and in the absence of stimulation by TNF-α (black columns). Changes of optical density are caused by TNF-α-activated expression of an alkaline phosphatase.

Results obtained with SEQ ID No. 3 on ODN 2006-stimulated HEK-Blue™ hTLR9 cells are shown in FIG. 3 and on TNF-α stimulated HEK-Blue™ TNF-α cells are shown in FIG. 4, respectively.

From this set of control experiments, it can be seen that the tested 10mer of SEQ ID No. 3 shows no TLR9 inhibitory effects but rather exhibits an independent and additive stimulatory effect on TLR 9 in the absence (cf. black bars in FIG. 3) or presence of the agonist ODN 2006 (cf. grey bars in FIG. 3). Again, no influence on the signal cascade is observed with the aptamer of SEQ ID No. 3 (cf. FIG. 4).

Example 3

As a control for the value and the validity of the assay used in Examples 1 and 2 above, an assay control using the established TLR 9 antagonist CpG ODN TTAGGG (SEQ ID No. 4: TTA GGG TTA GGG TTA GGG TTA GGG; MW of 7575 Da) in increasing concentrations (0, 30, 100, 300, 1000 and 3000 ng of TLR 9 antagonist; corresponding to 0, 3.96, 13.2, 39.6, 132 and 396 nM, respectively) instead of the aptamers of Example 1 or 2 was carried out as described above.

Figure 5:
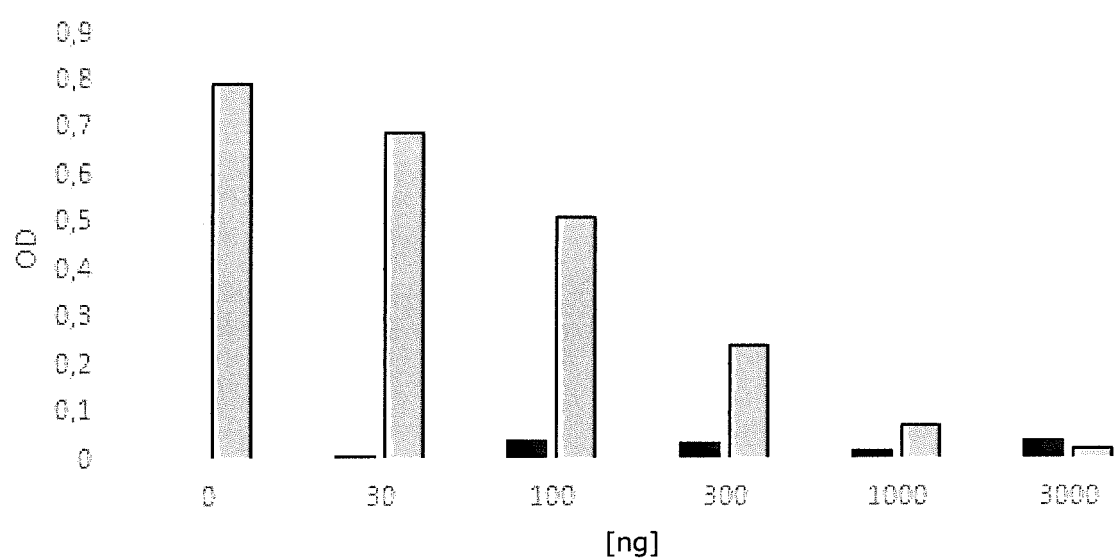
FIG. 5 shows the inhibition of TLR 9 activation in ODN 2006 (TLR 9 agonist)-stimulated HEK-Blue™ hTLR9 cells by adding increasing concentrations (in ng) of the TLR 9 antagonist CpG ODN TTAGGG (SEQ ID No. 4; depicted as grey columns). Potential intrinsic effects of increasing concentrations of CpG ODN TTAGGG (SEQ ID No. 4) on TLR 9 activation in the absence of stimulation by the TLR 9 agonist ODN 2006 (SEQ ID No. 2) were examined and are shown as black bars. Changes of optical density are caused by TLR 9-activated expression of an alkaline phosphatase.

Results obtained with the control antagonist on ODN 2006-stimulated HEK-Blue™ hTLR9 cells are shown in FIG. 5. As expected, the established TLR 9 antagonist was able to inhibit and/or suppress TLR 9 activation (cf. grey bars in FIG. 5) and did not cause a significant intrinsic effect in the absence of the TLR 9 agonist ODN 2006 (cf. black bars in FIG. 5).

The invention claimed is:

1. A method of treating a disease or disorder characterized by overexpression and/or overactivity of TLR9-mediated signaling in a subject, comprising administering to a mammalian subject in need an effective amount of an aptamer to inhibit activation of TLR9 in a cell of the subject, wherein the aptamer has a nucleic acid sequence of SEQ ID No.:1 (GGT TGG TGT GGT TGG) and/or a nucleic acid sequence being at least 80% identical to SEQ ID No.:1, and wherein the aptamer interacts specifically with the TLR 9 receptor to inhibit activation of TLR9 in the cell of the subject.

2. The method of claim 1, wherein the subject is a human.

3. The method of claim 1, wherein the method further comprises the previous step of determining that the subject to be treated is showing TLR9 overexpression and/or overactivity of TLR9-mediated signaling.

4. The method of claim 1, wherein the subject to be treated has previously tested positive for TLR9 overexpression and/or overactivity of TLR9-mediated signaling.

5. The method of claim 1, wherein the disease or disorder is selected from an autoimmune disorder, an inflammatory disorder, an autoimmune connective tissue disease (ACTD) and/or a neurodegenerative disorder, preferably the disorder is selected from psoriasis, rheumatoid arthritis, alopecia universalis, acute disseminated encephalomyelitis, Addison's disease, allergy, ankylosing spondylitis, antiphospholipid antibody syndrome, arteriosclerosis, atherosclerosis, autoimmune hemolytic anemia, autoimmune hepatitis, Bullous pemphigoid, Chagas' disease, chronic obstructive pulmonary disease, coeliac disease, cutaneous lupus erythematosus (CLE), dermatomyositis, diabetes, dilated cardiomyopathy (DCM), endometriosis, Goodpasture's syndrome, Graves' disease, Guillain-Barre syndrome, Hashimoto's disease, hidradenitis suppurativa, idiopathic thrombocytopenic purpura, inflammatory bowel disease, interstitial cystitis, morphea, multiple sclerosis (MS), myasthenia gravis, myocarditis, narcolepsy, neuromyotonia, pemphigus, pernicious anaemia, polymyositis, primary biliary cirrhosis, rheumatoid arthritis (RA), schizophrenia, Sjogren's syndrome, systemic lupus erythematosus (SLE), systemic sclerosis, temporal arteritis, vasculitis, vitiligo, vulvodynia, Wegener's granulomatosis, traumatic pain, neuropathic pain and acetaminophen toxicity, and tumour/cancer, wherein the tumour/cancer is selected from the group consisting of breast cancer, cervical squamous cell carcinoma, gastric carcinoma, glioma, hepatocellular carcinoma, lung cancer, melanoma, prostate cancer, recurrent glioblastoma, recurrent non-Hodgkin lymphoma, and colorectal cancer.

6. A method of inhibiting or suppressing activation of TLR9 in a cell comprising contacting a mammalian cell expressing TLR9 with an effective amount of an aptamer, wherein the method is carried out in vitro/ex vivo and wherein the aptamer has a nucleic acid sequence of SEQ ID No.:1 (GGT TGG TGT GGT TGG) and/or a nucleic acid sequence being at least 80% identical to SEQ ID No.:1, and wherein the aptamer interacts specifically with the TLR 9 receptor to inhibit activation of TLR9 in the cell of the subject.

7. The method of claim 6, wherein the method additionally comprises a previous step of testing the cell for TLR9 overexpression and/or overactivity of TLR9-mediated signaling.

8. The method according to claim 6, wherein the cell is a human cell.

9. The method of claim 1, wherein the aptamer is provided for administration in a pharmaceutical composition comprising the aptamer and at least one pharmaceutically acceptable excipient.

10. The method of claim 1, wherein the aptamer is provided prior to administration in a kit comprising the aptamer and a container.

11. The method of claim 3, wherein TLR9 overexpression and/or overactivity of TLR9-mediated signaling treatment in the subject is administered when TLR9-mediated production of TNFα is increased over a reference value for healthy subjects.

12. The method of claim 5, wherein a TNFα-specific ELISA test value for the subject to be treated is at least 50 pg/ml.

13. The method of claim 5, wherein a TNFα-specific ELISA test value for the subject to be treated is at least 75 pg/ml.

14. The method of claim 5, wherein a TNFα-specific ELISA test value for the subject to be treated is at least 100 pg/ml.

15. The method of claim 5, wherein a TNFα-specific ELISA test value for the subject to be treated is at least 125 pg/ml.

16. The method of claim 1, wherein the nucleic acid sequence is at least 85% identical to SEQ ID No.:1.

17. The method of claim 1, wherein the nucleic acid sequence is at least 90% identical to SEQ ID No.:1.

18. The method of claim 1, wherein the nucleic acid sequence is identical to SEQ ID No.:1.

19. The method of claim 6, wherein the nucleic acid sequence is at least 85% identical to SEQ ID No.:1.

20. The method of claim 6, wherein the nucleic acid sequence is at least 90% identical to SEQ ID No.:1.

21. The method of claim 6, wherein the nucleic acid sequence is identical to SEQ ID No. 1.

* * * * *